(12) United States Patent
Wasserman et al.

(10) Patent No.: US 6,542,180 B1
(45) Date of Patent: Apr. 1, 2003

(54) SYSTEMS AND METHODS FOR ADJUSTING LIGHTING OF A PART BASED ON A PLURALITY OF SELECTED REGIONS OF AN IMAGE OF THE PART

(75) Inventors: Richard M. Wasserman, Redmond, WA (US); Ana M. Tessadro, Seattle, WA (US)

(73) Assignee: Mitutoyo Corporation, Kawasaki (JP)

( * ) Notice: Subject to any disclaimer, the term of this patent is extended or adjusted under 35 U.S.C. 154(b) by 0 days.

(21) Appl. No.: 09/484,897

(22) Filed: Jan. 18, 2000

Related U.S. Application Data
(60) Provisional application No. 60/174,848, filed on Jan. 7, 2000.

(51) Int. Cl.[7] .................................................. H04N 7/18
(52) U.S. Cl. ..................................................... 348/131
(58) Field of Search ...................... 348/86–92, 125–134; 382/141–152; 345/327–328, 339, 343, 700, 716, 719, 723, 781, 803, 961

(56) References Cited

U.S. PATENT DOCUMENTS

| | | | | |
|---|---|---|---|---|
| 4,724,481 A | * | 2/1988 | Nishioka ..................... | 348/133 |
| 4,843,476 A | * | 6/1989 | Fujioka et al. .............. | 348/365 |
| 4,963,036 A | * | 10/1990 | Drisko et al. ................ | 382/172 |

(List continued on next page.)

*Primary Examiner*—Vu Le
(74) *Attorney, Agent, or Firm*—Oliff & Berridge, PLC

(57) ABSTRACT

The lighting behavior of a vision system is inconsistent between vision systems, within a vision system over time or between parts being viewed. This inconsistency makes it difficult to correctly run part programs even within a single run of parts on a single machine. The multi area image quality tool systems, methods and graphical user interfaces adjust the light intensity of a vision system to obtain a desired image quality or characteristic of a captured image. The multi area image quality tool is used to define a plurality of regions of interest within a captured image to be used to determine the image quality or characteristic of the captured image resulting from a current illumination level. The multi area image quality tool allows a user to easily and quickly define multiple regions of interest that can be used to determine the image quality of a captured image. The multi area image quality tool allows the user to specify the location, orientation and size of two or more regions of interest around a critical feature of the captured image, and to specify the light sources to be used to illuminate the part, the image quality to be measured, and a range of acceptable values for that image quality. Portions of the image are extracted based on the defined regions of interest. The image quality of the captured image is determined based on an analysis of the regions of interest and the image quality defined in the multi area image quality tool.

21 Claims, 7 Drawing Sheets

U.S. PATENT DOCUMENTS

| | | | | |
|---|---|---|---|---|
| 4,972,093 A | * | 11/1990 | Cochran et al. | 250/223 R |
| 5,051,825 A | * | 9/1991 | Cochran et al. | 348/131 |
| 5,153,668 A | * | 10/1992 | Katzir et al. | 356/237.2 |
| 5,166,985 A | * | 11/1992 | Takagi et al. | 348/128 |
| 5,298,989 A | * | 3/1994 | Tsukahara et al. | 348/126 |
| 5,454,049 A | * | 9/1995 | Oki et al. | 382/172 |
| 5,481,712 A | * | 1/1996 | Silver et al. | 345/810 |
| 5,519,496 A | * | 5/1996 | Borgert et al. | 348/126 |
| 5,588,068 A | * | 12/1996 | Longest et al. | 348/125 |
| 5,631,976 A | * | 5/1997 | Bolle et al. | 358/464 |
| 5,712,700 A | * | 1/1998 | Nagaishi et al. | 355/35 |
| 5,753,903 A | * | 5/1998 | Mahaney | 250/205 |
| 5,757,425 A | * | 5/1998 | Barton et al. | 348/241 |
| 5,850,472 A | * | 12/1998 | Alston et al. | 382/162 |
| 5,946,029 A | * | 8/1999 | Yoshimura et al. | 348/131 |
| 5,974,158 A | * | 10/1999 | Auty et al. | 382/103 |
| 6,091,847 A | * | 7/2000 | Chiu et al. | 348/125 |
| 6,108,036 A | * | 8/2000 | Harada et al. | 348/219 |
| 6,118,524 A | * | 9/2000 | King et al. | 250/559.34 |
| 6,169,816 B1 | * | 1/2001 | Ravkin | 382/128 |
| 6,198,529 B1 | * | 3/2001 | Clark, Jr. et al. | 356/237.5 |
| 6,201,880 B1 | * | 3/2001 | Elbaum et al. | 382/100 |
| 6,207,946 B1 | * | 3/2001 | Jusoh et al. | 250/208.1 |
| 6,272,204 B1 | * | 8/2001 | Amtower et al. | 378/63 |
| 6,282,462 B1 | * | 8/2001 | Hopkins | 700/259 |
| 6,303,916 B1 | * | 10/2001 | Gladnick | 250/205 |
| 6,304,050 B1 | * | 10/2001 | Skaar et al. | 318/568.11 |
| 6,316,950 B1 | * | 11/2001 | Denk et al. | 324/752 |
| 2002/0014577 A1 | * | 2/2002 | Ulrich et al. | 250/205 |

* cited by examiner

SYSTEMS AND METHODS FOR ADJUSTING LIGHTING OF A PART BASED ON A PLURALITY OF SELECTED REGIONS OF AN IMAGE OF THE PART

This application claims priority to co-pending U.S. Provisional Patent Application No. 60/174,848 filed Jan. 7, 2000.

BACKGROUND OF THE INVENTION

1. Field of the Invention

This invention relates to lighting systems for vision systems.

2. Description of Related Art

The light output of any device is a function of many variables. Some of the variables include the instantaneous drive current, the age of the device, the ambient temperature, whether there is any dirt or residue on the light source, the performance history of the device, etc. Machine vision instrument systems typically locate objects within their field of view using methods which may determine, among other things, the contrast within the region of interest where the objects may be found. To some degree, this determination is significantly affected by the amount of incident light or transmitted light.

Automated video inspection metrology instruments generally have a programming capability that allows an event sequence to be defined by the user. This can be implemented either in a deliberate manner, such as programming, for example, or through a recording mode which progressively learns the instrument sequence. The sequence commands are stored as a part program. The ability to create programs with instructions that perform a sequence of instrument events provides several benefits.

For example, more than one workpiece or instrument sequence can be performed with an assumed level of instrument repeatability. In addition, a plurality of instruments can execute a single program, so that a plurality of inspection operations can be performed simultaneously or at a later time. Additionally, the programming capability provides the ability to archive the operation results. Thus, the testing process can be analyzed and potential trouble spots in the workpiece or breakdowns in the controller can be identified. Without adequate standardization and repeatability, archived programs vary in performance over time and within different instruments of the same model and equipment.

Conventionally, as illustrated in U.S. Pat. No. 5,753,903 to Mahaney, closed-loop control systems are used to ensure that the output light intensity of a light source of a machine vision system was driven to a particular command level. Thus, these conventional closed-loop control systems prevent the output light intensity from drifting from the desired output light intensity due to variations in the instantaneous drive current, the age of the light source, the ambient temperature, or the like.

SUMMARY OF THE INVENTION

This invention is especially useful for producing reliable and repeatable results when using predetermined commands to the illumination system, such as when the command is included in a part-program that will be used on a different vision system, and/or on the same or a different vision system at a different time or place, or to view parts having variable surface characteristics.

In these conventional closed-loop control systems, the output light intensity of the light sources is driven to the particular command level regardless of the resulting quality of the illumination of the part obtained by driving the light source to the particular command level. However, even if the output light intensity of the light source is controlled to a particular command level, the resulting image captured by the machine vision system may not have a desired image quality or characteristic.

Similarly, U.S. patent application Ser. No. 09/425,990, filed Dec. 30, 1999, discloses a system for calibrating the output intensity of a light source so that the actual output light intensity of the light source in operation corresponds to the desired output light intensity based on the particular input light intensity command value. Again, even though the output light intensity may be at the desired value, the image quality or characteristic of the resulting captured image may be insufficient.

Additionally, input light settings in many vision systems often do not correspond to fixed output light intensities. Moreover, the output light intensity can not be measured directly by the user. Rather, the output light intensity is measured indirectly by measuring the brightness of the image. In general, the brightness of the image is the average gray level of the image. Alternatively, the output light intensity may be measured directly using specialized instruments external to a particular vision system.

In any case, the lighting behavior, i.e., the relationship between the measured output light intensity and the commanded light intensity, is not consistent between vision systems, within a single vision system over time or between parts being viewed. Rather, the relationship between the measured output light intensity and the commanded light intensity depends on the optic elements of the vision system, the particular light source being used to illuminate a part, the particular bulb of that light source, the particular part being viewed and the like.

This inconsistency of the lighting behavior makes it difficult to correctly run part-programs even within a single run of parts on a single machine. That is, a part program with a fixed set of commanded light intensity values might produce images of varying brightness when illuminating different pieces of a single part. However, many measurement algorithms, such as algorithms using edge detection, depend on the brightness of the image. As a result, because the brightnesses of resulting images generated when viewing different parts are often different, part programs do not run consistently.

This invention provides systems, methods and graphical user interfaces that adjust the light intensity of a vision system to obtain a desired image quality or characteristic of a captured image.

This invention separately provides systems, methods and graphical user interfaces that define a plurality of regions of interest within a captured image to be used to determine the image quality or characteristic of the captured image resulting from a current illumination level.

This invention separately provides systems, methods and graphical user interfaces that allow a user to easily and quickly define multiple regions of interest that can be used to determine the image quality of a captured image.

In various and exemplary embodiments of the systems, methods and graphical user interfaces of this invention, a user can invoke a multi area image quality tool to define two or more regions of interest within a captured image of a part. This multi area image quality tool is invoked during generation of a part program useable to illuminate the part and to capture images of the part for subsequent analysis. The multi area image quality tool allows the user to specify the location, orientation, size and separation of the two or more regions of interest. The multi area image quality tool also allows the user to specify one or more of the light sources to be used to illuminate the part and possibly the angle from which the illumination is provided, the operational mode of the lighting sources of the vision system, the image quality to be measured within the two or more regions of interest and how the image portions within the region of interest are to be analyzed, including either a goal to be reached for the selected image quality, and/or a range of acceptable values for the selected image quality.

In operation of the part program which includes an instance of the multi area image quality tool, the part is illuminated based on the illumination commands contained within the part program immediately preceding that instance of the multi area image quality tool. In particular, either the closed-loop control systems disclosed in, for example, the 903 patent, or the calibration systems and methods disclosed in the incorporated 104751 application, can be used to ensure the initial illumination level correctly corresponds to the desired illumination level. The vision system then captures an image of the part using this initial illumination level. Portions of the image are extracted based on the defined regions of interest. The image quality of the captured image is determined based on an analysis of the regions of interest and the image quality defined in this instance of the multi area image quality tool.

If the image quality has reached the defined goal and/or falls within the range defined within this instance of the multi area image quality tool, the next instruction in the part program is executed. Otherwise, if the image quality is not within the defined range, the intensity of the light source is adjusted. Then, a new image of the part is captured and the region of interest portions of the new captured image are extracted and analyzed. This procedure is repeated until the current output intensity of the light source results in the captured image of the part having an image quality in the regions of interest that falls within the defined range. Thus, by using the systems, methods and graphical user interfaces of this invention, the user can define the desired image quality, rather than the desired illumination level, that should be used to obtain the captured image of the part.

These and other features and advantages of this invention are described in or are apparent from the following detailed description of the preferred embodiments.

BRIEF DESCRIPTION OF THE DRAWINGS

The preferred embodiments of this invention will be described in detail, with reference to the following figures, wherein.

DETAILED DESCRIPTION OF THE EXEMPLARY EMBODIMENTS

The lighting adjusting systems, methods and graphical user interfaces of this application are useable in conjunction with the lighting calibration systems and methods disclosed in the U.S. patent Ser. No. 09/425,990, herein incorporated by reference in its entirety.

Figure 1:
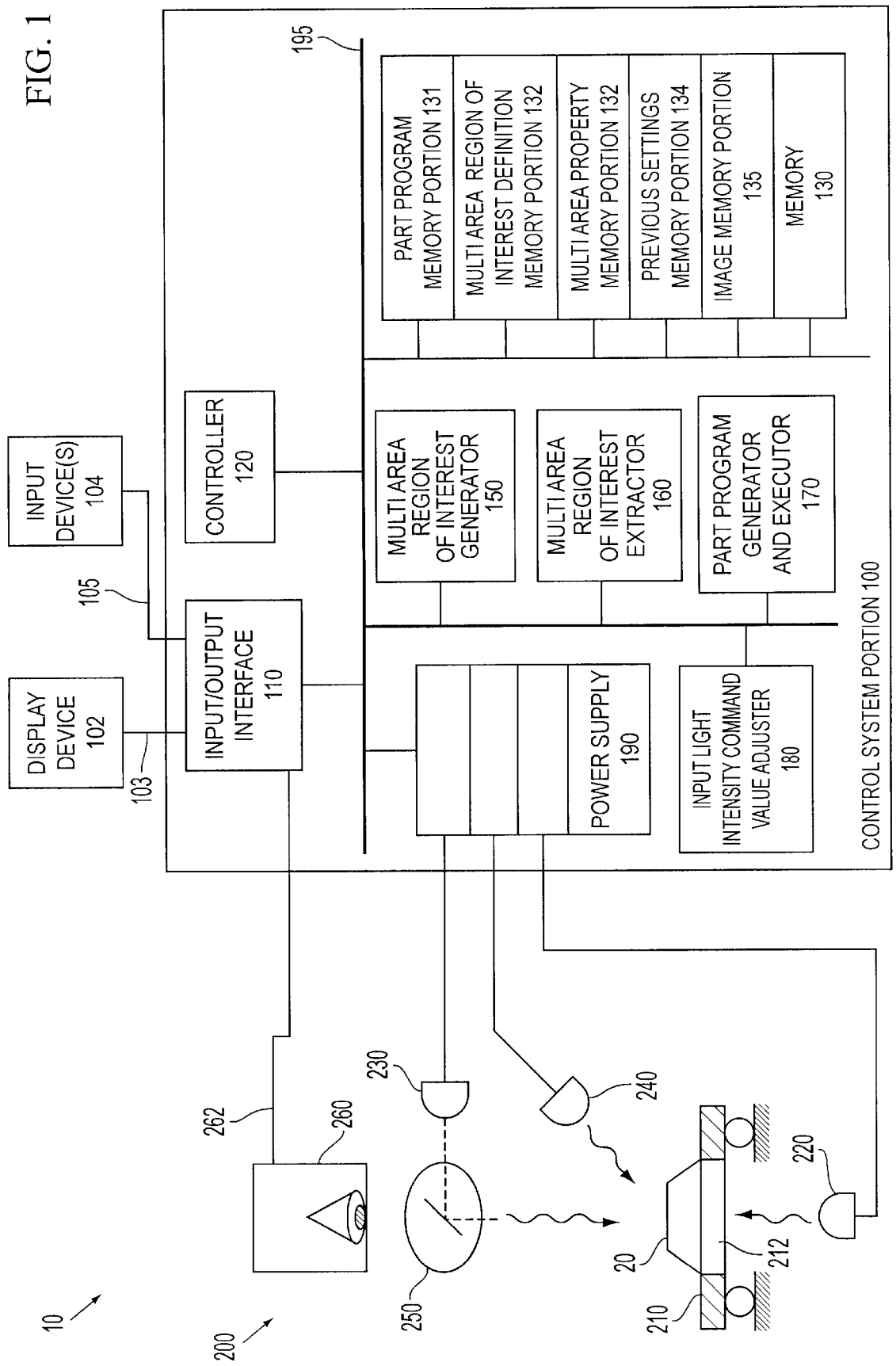
FIG. 1 shows one exemplary embodiment of a vision system using one exemplary embodiment of a light intensity control system according to this invention.

For simplicity and clarification, the operating principles, and design factors of this invention are explained with reference to one exemplary embodiment of a vision system according to this invention, as shown in FIG. 1. The basic explanation of the operation of the vision system shown in FIG. 1 is applicable for the understanding and design of any vision system that incorporates the lighting adjusting systems and methods according to this invention.

As used herein, the input light intensity command value is the light intensity value set by the user to control the light output intensity of the source light. The input light intensity command value is set either expressly in a part program or using a user interface. The range of the input light intensity command value is between zero and one, which represents a percentage of the maximum output intensity possible. In the following description, the ranges 0–1 and 0%–100% are used interchangeably. It should be appreciated that zero or 0% corresponds to no illumination, while 1 or 100% corresponds to full illumination.

As used herein, the output light intensity value is the intensity of the light source of the vision system as delivered to the part and received by the optical sensor of the vision system after passing back and forth through the optical elements of the vision system. In various exemplary embodiments of the lighting adjusting systems, methods and graphical user interfaces of this invention, the output light intensity value 1 is measured using an average gray level of a region of the image.

In the following description of various exemplary embodiments of the systems and methods according to this invention, the operation of these various exemplary embodiments of the systems and methods is outlined with the understanding that most system operations and method steps, such as, for example, the generation and execution of part program instructions, are performed automatically. It should be appreciated that manual performing such system operations and method steps is also within the scope of this invention.

FIG. 1 shows one exemplary embodiment of a vision system incorporating one exemplary embodiment of a lighting adjusting control system according to this invention. As shown in FIG. 1, the vision system 10 includes a control portion 100 and a vision system components portion 200. The vision system components portion 200 includes a stage 210 having a central transparent portion 212. A part 20 to be imaged using the vision system 10 is placed on the stage 210. Light emitted by one or more of the light sources 220–240 illuminates the part 20. The light from the one or more light sources 220–240 passes through a lens system 250 after illuminating the part 20, and possibly before illuminating the part 20, and is gathered by a camera system 260 to generate an image of the part 20. The image captured by the camera system 260 is output on a signal line 262 to the control portion 100. The light sources 220–240 used to illuminate the part 20 include a stage light 220, a coaxial light 230, and a surface light 240, such as a ring light or a programmable ring light.

The distance between the stage 210 and the camera system 260 can be adjusted to change the focus of the image of the part captured by the camera system 260. In particular, in various exemplary embodiments of the vision system 10, the position of the camera system 260 along a vertical axis is changeable relative to a fixed stage 210. In other various exemplary embodiments of the vision system 10, the position of the stage 210 along the vertical axis can be changed relative to a fixed camera system 260. In further various exemplary embodiments of the vision system 10, the vertical positions of both the camera system 260 and the stage 210 can be altered to maximize the focus range of the vision system 10.

As shown in FIG. 1, one exemplary embodiment of the control portion 100 includes an input/output interface 110, a controller 120, a memory 130, a multi area region of interest generator 150, a multi area region of interest extractor 160, a part program generator and/or executor 170, an input light intensity command value adjuster 180, and a power supply 190, each interconnected either by a data/control bus 195 or by direct connections between the various elements. The signal line 262 from the camera system 260 is connected to the input/output interface 110. Also connected to the input/output interface 110 can be a display 102 connected over a signal line 103 and one or more input devices 104 connected over one or more signal lines 105. The display 102 and the one or more input devices 104 can be used to view, create and modify part programs, to view the images captured by the camera system 262 and/or to directly control the vision system components 200. However, it should be appreciated that, in a fully automated system having a predefined part program, the display 102 and/or the one or more input devices 104, and the corresponding signal lines 103 and/or 105, may be omitted.

As shown in FIG. 1, the memory 130 includes a part program storage portion 131, a multi area region of interest definition memory portion 132, a multi area property memory portion 133, a previous settings memory portion 134, and a captured image storage portion 135. The part program memory portion 131 stores one or more part programs used to control the operation of the vision system 10 for particular types of parts. The image memory portion 135 stores images captured using the camera system 260 when programming and/or operating the vision system 10.

The multi area region of interest definition memory portion 132 contains data defining the location of the multi area image quality tool within the captured image, as well as the width and height of a rectangular bounding box of the multi area image quality tool that encompasses the two or more regions of interest forming the multi area image quality tool and the angle that the multi area image quality tool makes with a predetermined axis of the captured image. These features of the multi area image quality tool will be described in greater detail with respect to FIG. 2.

The multi area property memory portion 133 stores, for at least a current multi area image quality tool, data identifying the light source or sources that will be adjusted to obtain the desired image quality, data defining the operation mode for operating the various light sources of the vision system 10, data defining the image quality that is to be used as the metric for determining whether the identified light source(s) to be adjusted need further adjusting, data defining the tolerance range for the selected image quality, and data defining whether the image data in the regions of interest is to be filtered. The various properties of the multi area image quality tool will be described in greater detail with respect to FIGS. 2–6.

The previous settings memory portion 134 stores previous settings for the various light sources 220–240 of the vision system 10 that were in place prior to the part program executing the multi area image quality tool to adjust one or more of the light sources 220–240 of the vision system 10. In general, these settings would have been defined in previously executed portions of the part program.

Figure 2:
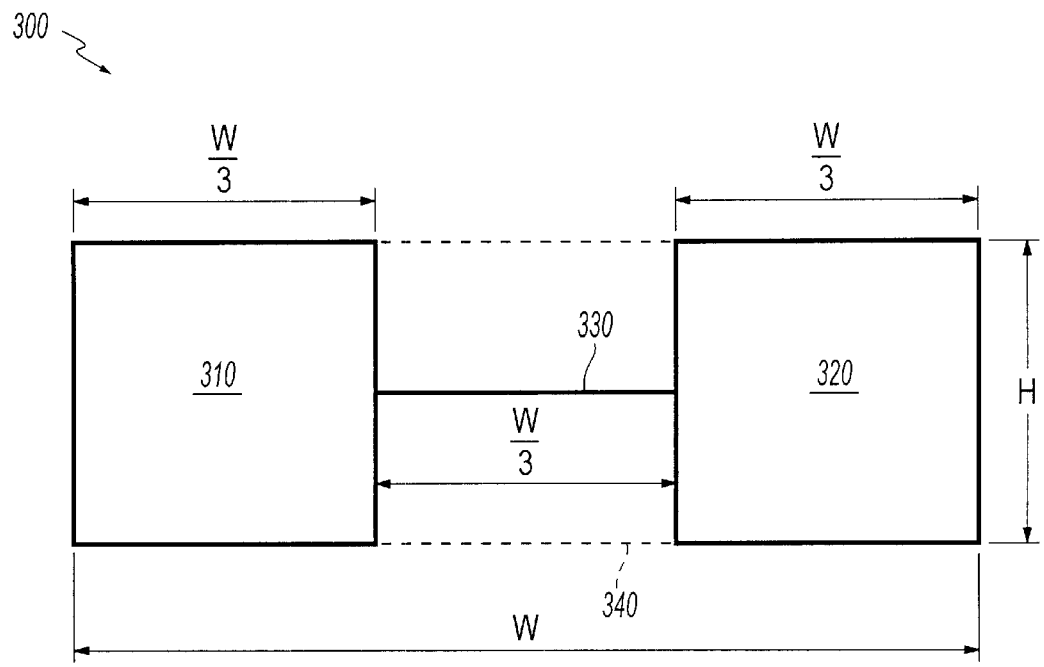
FIG. 2 shows a first exemplary embodiment of a multi area image quality tool widget according to this invention and of the dimensioning of the two regions of interest and their relative spacing.

FIG. 2 shows one exemplary embodiment of a multi area image quality tool 300 according to this invention. In particular, the exemplary embodiment of the multi area image quality tool 300 shown in FIG. 2 is a dual area image quality tool 300. As shown in FIG. 2, the dual area image quality tool 300 includes a first region of interest 310 and a second region of interest 320 connected by a bar 330. The dual area image quality tool 300 is thus bound by a rectangle 340. In the first exemplary embodiment of the dual area image quality tool 300, the dual area image quality tool 300 has two regions of interest 310 and 320. However, it should be appreciated that any number of regions of interest could be provided within the multi area image quality tool according to this invention.

As indicated above, the multi area region of interest definition memory portion 132 includes data defining the location of the dual area image quality tool 300 within a captured image. This data includes a horizontal distance or offset from an origin point of the captured image and a vertical distance or offset from the origin point of the captured image. It should be appreciated that the horizontal and vertical distances from the origin of the captured image can be linked to any arbitrary point within the rectangle 340 occupied by the multi area image quality tool 300. However, in general, the horizontal and vertical distances will be linked to one of the corners of the rectangle 340 or to the center point of the rectangle 340.

As also indicated above, the multi area region of interest definition memory portion 132 stores the height and width data defining the height and width of the rectangle 340 that bounds the multi area image quality tool 300. In various exemplary embodiments of the multi area image quality tool 300, as in the exemplary embodiment of the dual area image quality tool 300 shown in FIG. 2, once the height and width are defined, the regions of interest 310 and 320 are defined as rectangles having a height equal to the height of the rectangle 340 and widths equal to one-third of the width of the rectangle 340. That is, each of the region of interests 310 and 320 occupies one-third of the width of the rectangle 340, while the linking bar 330 occupies the remaining third.

It should be appreciated that, in other various exemplary embodiments of the multi area image quality tool according to this invention, different ratios for the width of the regions of interest and the linking bar or bars can be used. It should be appreciated that the length of the linking bar can be zero. That is, two regions of interest can be placed immediately adjacent to each other and right to the edge of the critical feature such as an edge. In addition, in yet further exemplary embodiments of the multi area image quality tool according to this invention, the multi area region of interest definition memory portion 132 can contain additional data that is supplied by the user or that is automatically generated to actively determine the ratios of the regions of interest to the linking bars.

As further indicated above, the multi area region of interest definition memory portion 132 also includes angle data that defines the angle made by the width axis of the rectangle 340 to a predetermined axis within the captured image. Thus, if this predetermined axis of the captured image is aligned with the horizontal axis of the captured image, an angle of 0° corresponds to the width of the rectangle 340 extending along the horizontal axis of the captured image, while an angle of 90° or 270° indicates that the width axis of the rectangle 340 extends along the vertical axis of the captured image. In general, the rectangle 340 will be rotated about the same point of the rectangle 340 as is associated with the horizontal and vertical distances. Thus, if the horizontal and vertical distances are linked to the center point of the rectangle 340, the rectangle 340 will be rotated about the center point.

In operation, when a user uses the vision system 10 to create a part program, the user generates part program instructions either by explicitly coding the instructions using a part programming language or by generating the instructions by moving the vision system 10 through a training sequence such that the part program instructions capture the training sequence. In particular, these instructions will cause the vision system to manipulate the stage 210 and/or the camera system 260 such that a particular portion of the part 20 is within the field of view of the camera system 260 and at a desired focus state. It should also be appreciated that, prior to capturing the image, the user will generate part program instructions that activate one or more of the light sources 220–240 to provide a desired illumination of the part 20.

The part program generator and/or executor 170 will then, under control of the controller 120, command the camera system 260 to capture an image of the part 20 and output the captured image to the control system 100. The control system 100 will then, under control of the controller 120, input the captured image through the input/output interface 110 and store the captured image in the captured image storage portion 135 of the memory 130. The controller 120 will then display the captured image on the display device 102.

Next, in accordance with the systems, methods and graphical user interfaces of this invention, the user will access the multi area image quality tool, in general by using a graphical user interface. That is, the user will activate a multi area image quality tool generation menu item or tool bar button. The user will then select a portion 340 of the captured image. In response, an instance of the multi area image quality tool 300 will be placed within the selected portion 340. In particular, in various exemplary embodiments, a part program instruction can be generated that defines the horizontal and vertical distances of the origin point of the multi area image quality tool 300 from the origin of the captured image, the height and width of the selected region 340 and the angle the selected region 340 makes with the predetermine zero angle axis. Different embodiments of the multi are image quality tool, as illustrated in FIGS. 3–6, will result in different types of part program instructions to be generated that define different types of information that is appropriate to a particular different embodiment.

Figure 3:
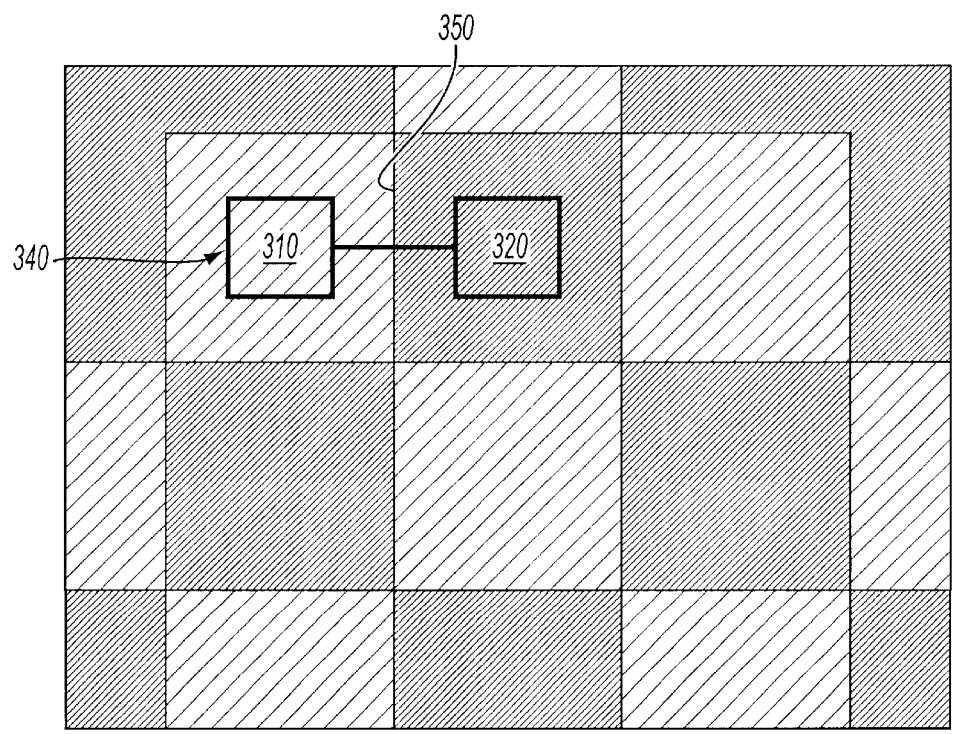
FIG. 3 is a portion of a first exemplary image and the first exemplary embodiment of the multi area image quality tool graphical user interface widget used to select the two or more regions of interest that surround a critical region.

If the control system 100 automatically scales the proportions of the regions of interest within the multi area image quality tool 300, the two or more regions of interest will be automatically located within the selected region 340 and one or more bars will be drawn between the determined regions of interest. In general, the selected region 340 will be selected such that the two or more regions of interest are positioned on different sides of a selected feature within the captured image, such as an edge, such that one or more of the connecting bars extend across the selected feature. For example, as shown in FIG. 3, the dual area contrast area tool 300 having two regions of interest 310 and 320 is drawn such that the selected region 340 extends across an edge 350. Thus, the region of interest 310 is located within the lighter region 352, while the other region of interest 320 is located within the darker region 352 and the bar 330 extends across the edge 350.

FIG. 3 shows a portion of a first exemplary image and the first exemplary embodiment of the multi area image quality tool and graphical user interface widget 300 used to select the two or more regions of interest that surround a critical region 350. In FIG. 3, the portions of the captured image within the regions of interest 310 and 320 have generally constant image values. Thus, filtering is generally not needed for these regions of interest.

In many cases, it may be true that the regions of interest each have constant image values. However, more precisely, each region of interest 310 and 320 is typically homogenous relative to the particular image quality or characteristic that has been selected. Most commonly, this generally means, at a minimum, that the visual texture is consistent within that region of interest. For example, the pixel values within a region of interest representing a magnified view of a piece of brushed aluminum would probably vary significantly within a region of interest. However, there generally would not be any sudden changes in the overall texture within that region of interest. This type of homogeneity is visible in the left side of FIG. 4. However, it should be appreciated that there can be sharp discontinuities within a region of interest without rendering such regions of interest unusable.

Figure 4:
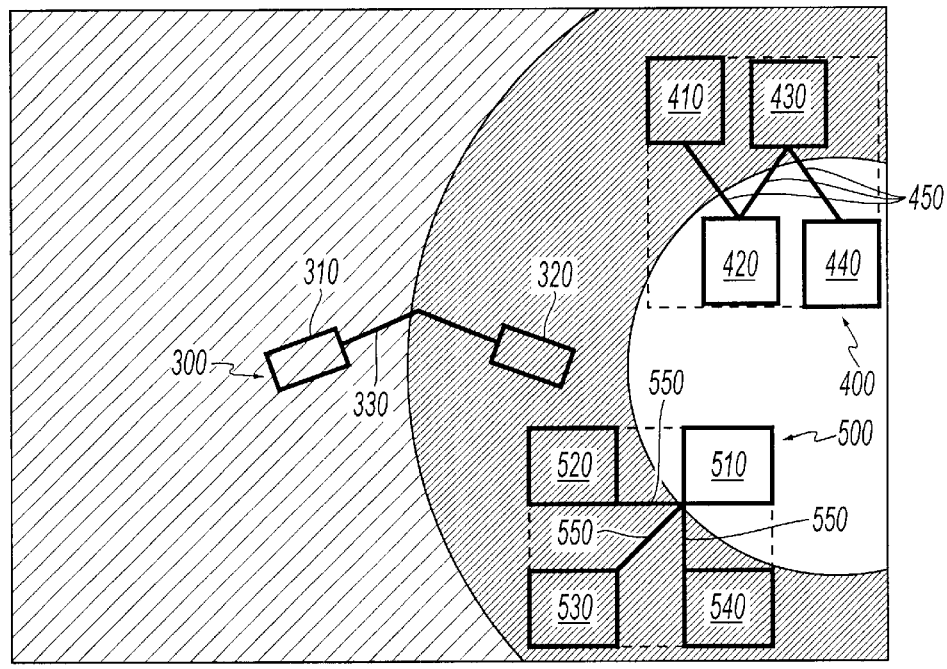
FIG. 4 shows a portion of a second exemplary embodiment of an image and second-fourth exemplary embodiment of the multi area image quality tool.

FIG. 4 shows two multi area image quality tools 400 and 500 that each have more than two regions of interest and a dual area image quality tool 300 having a bent bar 330. In particular, a second exemplary embodiment of the multi area image quality tool 400 includes four regions of interest 410–440 that are chained together. In contrast, a third exemplary embodiment of the multi area image quality tool 500 includes four regions of interest 510–540, where the second-fourth regions of interest 520–540 are each connected to the first region of interest 510. The fourth exemplary embodiment of the dual area image quality tool 300 shown in FIG. 4 clarifies that the regions of interest do not have to be co-linear, but can be at angled relative to each other.

The second and third exemplary embodiments of the multi area image quality tools 400 and 500 thus illustrate the two general methods for linking the various regions of interest with the bars 450 and 550. In the first method, the various regions of interest are connected in series, with the second region of interest connected to the first region of interest, the third region of interest connected to the second region of interest, and so on. In the second method, the various regions of interest are connected in parallel, with each of the second, third, etc., regions of interest connected to the first region of interest.

When the multi area image quality tool contains more than two regions of interest, the multi-area properties for that multi area image quality tool additionally indicates one or more of the total number of regions of interest for that multi area image quality tool, the method in which the regions of interest are connected, the angle between the bars connecting the regions of interest and the like.

Figure 5:
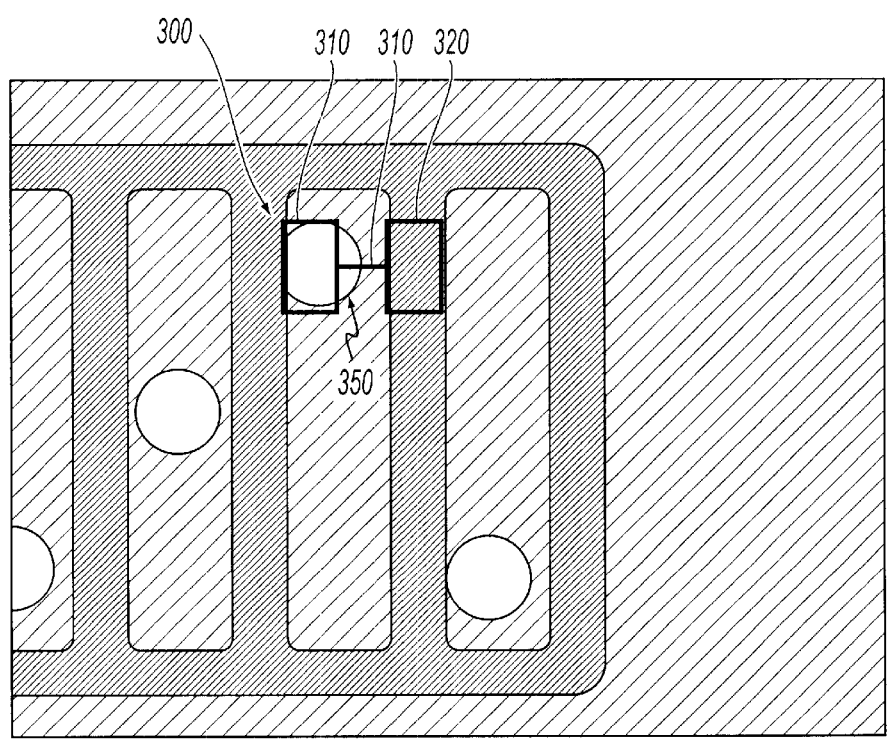
FIG. 5 shows a portion of a third exemplary embodiment of an image and the first exemplary embodiment of the multi area image quality tool.

FIG. 5 shows a portion of a third exemplary embodiment of an image and the first exemplary embodiment of the multi area image quality tool. In FIG. 5, the image values within the region of interest 310 include both very bright areas and very dark areas. Thus, filtering the regions of interest 310 and 320 to remove these extreme image values should improve the analysis of the selected image quality.

Figure 6:
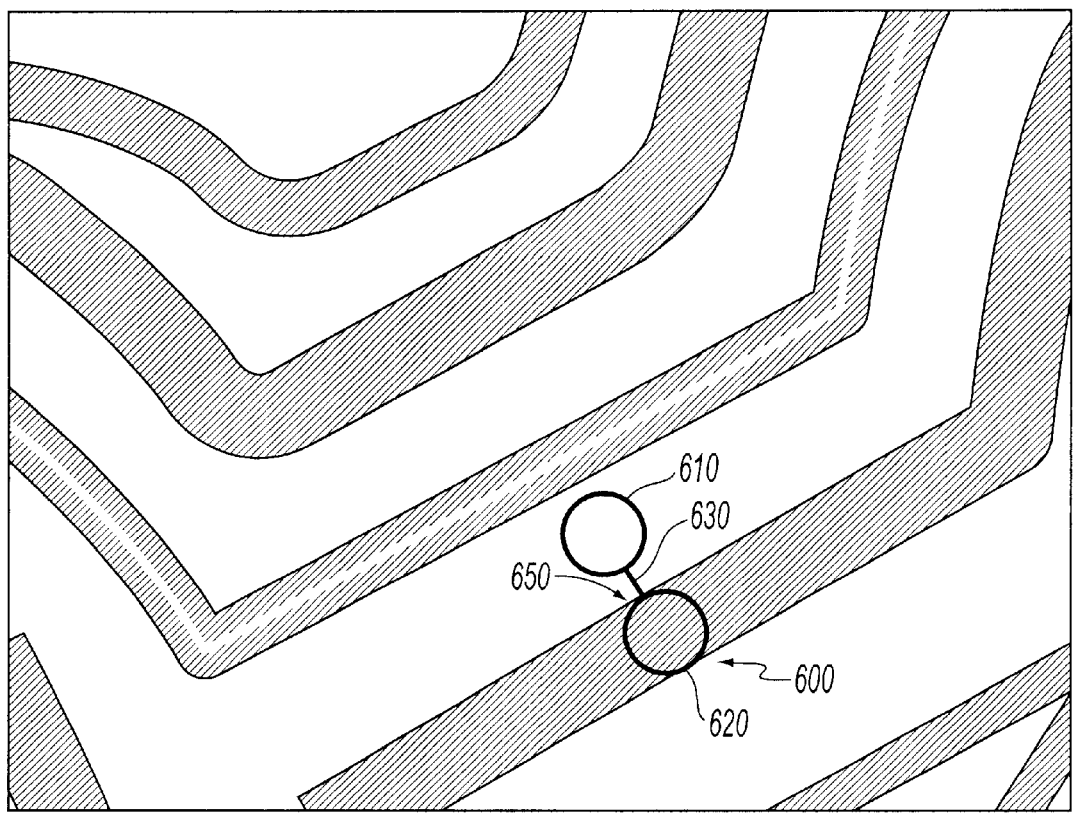
FIG. 6 shows a portion of a fourth exemplary embodiment of an image and a fifth exemplary embodiment of a multi area image quality widget according to this invention.

FIG. 6 shows a portion of a fourth exemplary embodiment of an image and a fifth exemplary embodiment of a multi area image quality tool and graphical user interface widget 600 according to this invention. In particular, in FIG. 6, the multi area image quality tool 600 uses circular rather than rectangular shaped regions of interest 610 and 620. In general, the shape of the regions of interest is not critical. However, the shape of the regions of interest can be selected to match the underlying shapes of the selected portions of the captured image. Additionally, in FIG. 6, the multi area image quality tool 600 is shown rotated at an angle so that the critical feature 650 extends perpendicularly across the bar 630.

It should also be appreciated that the user can manipulate the region 340 to change the height, width, angle or the location of the region 340 to insure that the regions of interest 310 and 320 include the proper portions of the captured image and/or to ensure that the bar 330 extends across the critical feature, such as the edge 350. Once the user is satisfied that the multi area image quality tool 300 is properly positioned, the user indicates this to the control system 100. In response, the part program generator and/or executor 170 generates a part program instruction based on the current state of the multi area image quality tool 300.

Then, the user indicates which one of the various lighting sources 220–240 will be controlled to adjust its output based on the particular image quality. For example, for the vision system 10 shown in FIG. 1, the lighting source data of the multi area property data for this instance of the multi area image quality tool can indicate that the stage light 220 is to be used as the light source to be adjusted, the coaxial light 230 is to be used as the light source to be adjusted, or the ring light 240, or all the portions of a programmable ring light 240, if provided, are to be used as the light source to be adjusted. Additionally, the lighting source data can indicate that only some of the various programmable portions of the programmable ring light 240 are to be adjusted. In this case, the multi area property data for the current multi area image quality tool will also include data that defines the particular ones of the portions of the programmable ring light that are to be controlled.

The multi area property data also includes data that indicates which image quality or characteristic is to be used when adjusting the selected light source. In various exemplary embodiments of the systems, methods and graphical user interfaces according to this invention, the various image qualities or characteristics that can be used include the contrast, the average brightness, the median brightness, the brightness mode and the like. However, it should be appreciated that any image characteristic or quality that is dependent on the output light intensity of the selected light source can be used.

In various exemplary embodiments, the multi area property data associated with the current instance of the multi area image quality tool also includes a goal state that defines the goal for the selected image quality or characteristic and a failure threshold. The goal state is, for example, when the image quality is contrast, a maximum contrast or a minimum contrast. The failure threshold defines an error state that causes the part program to end. For example, when the goal state is maximum contrast, the failure threshold indicates the value that the maximum threshold must reach for the part program to continue executing.

In various other exemplary embodiments, the multi area property data associated with the current instance of the multi area image quality tool also includes a tolerance value for the selected image quality. This tolerance value indicates the range of image quality values that are acceptable and thus require no further adjustment of the selected light source(s). In particular, the tolerance value can define a minimum quality difference in the portions of the captured image within the regions of interest of the multi area image quality tool, a maximum difference, or both a minimum and maximum difference.

For example, if the selected image quality is average brightness, the portions of the captured image within the regions of interest 310 and 320 will be analyzed to determine the average brightness within each of the regions of interest 310 and 320. Then, the difference is determined between the average brightness for each of the regions 310 and 320. That is:

$$C = |M_1 - M_2|, \tag{1}$$

where:
C is the contrast;
$M_1$ is the mean image intensity in the first region of interest; and
$M_2$ is the mean image intensity in the second region of interest.

In various exemplary embodiments, the determined difference is analyzed to determine if it is at, or has reached, a goal state. Once the defined goal state is obtained and exceeds the failure threshold, the next part program instruction can be performed. Otherwise, if the failure threshold is not exceeded, execution of the part program halts.

In the various other exemplary embodiments, the determined difference is compared to the tolerance value to determine if the difference is greater than a minimum value for a minimum tolerance value, less than a maximum value for a maximum tolerance value, or between the minimum and maximum values if both are defined. Once the defined tolerance value is obtained, the next part program instruction can be performed.

In various exemplary embodiments of the systems and methods of this invention, a numerical target value for the image quality or characteristic is established by manual training. That is, the user manually operates the machine in training mode, and establishes the target value, for example, by adjusting the light sources, until the user's subjective evaluation of the image quality in the critical region is favorable. Then a value or values corresponding to the image quality or characteristic is determined from the current, subjectively favored, image data. That value then becomes the numerical target value stored for reference during future automatic execution of the part program. For example, for an image characteristic related to contrast in the image, Eq. 1 outlined above can be used.

Eq. 1 can provide a numerical value that will tend to correspond to the light intensity gradient between two properly located regions of interest. If an edge is located between these two regions of interest, i.e., in the critical region, then this numerical value and the corresponding light intensity gradient will correspond to image characteristics which influence most edge-location determining algorithms. Thus, reproducing a particular numerical value of this type will tend to reproduce an image of the edge which will tend to lead to a reproducible edge-location calculated from the image data.

Alternatively, or in addition, the user may perform an iterative procedure including an additional operation in the critical region to replace or supplement the subjective acceptance of the light settings during manual training. For example, after setting the input light intensity command values and determining the resulting value for the image quality or characteristic, the user may determine the location of an edge in the critical region by well-established methods and store the location for future reference. Then the user can adjust the light sources to slightly different input light intensity command values, determine a new value, or values, corresponding to the image characteristic from the current image data, and again perform the additional operation, such as determining the location of an edge, in the critical region.

Since the ultimate goal of setting the input light intensity command values for the light sources is to determine the edge location reliably and repeatably, the user may analyze the resulting edge location data to determine which numerical values corresponding to the image characteristic correspond to acceptable edge location values, i.e., values which are determined to be within an acceptable accuracy range. This method can be used to establish the best numerical target value for the image characteristic, as well as the tolerance range for the numerical target value of the of the image characteristic.

It should be appreciated that two additional multi area property values can be defined. An operation mode value indicates whether the selected image quality will be determined based solely on the illumination provided by the selected light source or whether the selected image quality will be determined based on all of the light sources that are currently active.

The second value indicates whether the image data within the regions of interest should be filtered to exclude pixels having extreme image quality values. For example, if the image quality is based on brightness, the filter can be used to exclude unusually bright or unusually dark pixels when determining whether the determined image quality is within the selected tolerance value.

Once the user has defined the dimensional data defining the multi area image quality tool and the data defining the properties to be used when using the defined multi area image quality tool, and the corresponding part program instructions have been added to the part program being generated, the user can then generate the next part programming instruction, which can be an instruction to create another multi area image quality tool. The user continues in this manner until the part program has been completely generated and stored in the part program memory 131.

When the vision system 10 receives a command to execute a part program stored in the part program memory portion 131, the part program generator and/or executor 170, under control of the controller 120, begins reading instructions of the part program stored in the part program memory portion 131 and executing the read instructions. In particular, the instructions may include commands to turn on or otherwise adjust one or more of the light sources 220–240. In particular, such a command will include an input light intensity command value.

When the part program generator and/or executor 170 encounters such a light source instruction, the part program generator and/or executor 170 outputs the input light intensity command value instruction to the input light intensity command value adjuster 180. The input light intensity command value adjuster 180, under control of the controller 120, outputs the initial input intensity command value to the power source 190, while the part program generator and/or executor 170 outputs a command to the power source 190 identifying the light source or sources 220–240 to be driven. The power source 190 then drives the identified light source or sources 220–240 based on the initial input light intensity command value by supplying a current signal over one or more of the signal lines 222, 232 or 242 to the appropriate one or more of the light sources 220–240 of the vision system components 200.

For part programs that include instructions related to the multi area image quality systems, methods and graphical user interfaces according to this invention, the part program generator and/or executor 170 will eventually read an instruction that defines the location, size and angle of a multi area image quality tool according to this invention. In response, the part program generator and/or extractor 170, under control of the controller 120, stores the multi area image quality tool definition data in the multi area region of interest definition memory portion 132, and the multi area property data in the multi area property memory portion 133.

The input light intensity command value adjuster 180, under control of the controller 120, accesses the multi area property data stored in the multi area property memory portion 133 to determine whether the selected image quality is to be determined based solely on the illumination provided by the selected light source or whether the selected image quality is to be determined based on all of these light sources that are currently active. If the selected image quality will be determined based on all of the light sources that are currently active, the input light intensity command value adjuster indicates to the multi area region of interest extractor 160 that the regions of interest can be extracted from the current captured image.

In contrast, if the selected image quality is to be determined based solely on the illumination provided by the selected light source, the input light intensity command value adjuster 180 first stores the current settings for the active ones of the light sources 220–240 in the previous settings memory portion 134. The light intensity command value adjuster 180 then turns off any other light sources that may currently be active. The controller 120 then provides a signal to the camera system 260 through the input/output interface 110 and the signal line 262. In response, the camera system 260 then captures a new image that is illuminated solely by the light source to be adjusted and outputs the newly captured image over the signal line 262 to the control system 100. The input/output interface 110, under control of the controller 120 stores the newly captured image in the image memory portion 135 of the memory 130.

The multi area region of interest generator 150 then reads the multi area region of interest definition stored in the multi area region of interest definition memory portion 132 to define the dimensions of the various regions of interest defined within the multi area contrast instruction. The multi area region of interest extractor 160 then extracts image data from the current captured image corresponding to the regions of interests generated by the multi area region of interest generator 150 at the locations indicated by the multi area region of interest generator 150.

In various exemplary embodiments, the multi area region of interest extractor 160 accesses the multi area property data stored in the multi area property memory portion 133 to determine the image quality or characteristic that the extracted portions of the captured image are to be analyzed for and to determine the goal state that the determined image quality or characteristic is to be driven to. The multi area region of interest extractor 160 then generates the defined image quality or characteristic and determines if the determined image or quality of characteristic indicates, relative to the goal state, whether the light source defined by the multi area property data stored in the multi area property memory portion 133 needs to be adjusted. If not, the multi area region of interest extractor 160 indicates to the part program generator and/or executor 170 that the next part program instruction should be executed.

In other various exemplary embodiments, the multi area region of interest extractor 160 accesses the multi area property data stored in the multi area property memory portion 133 to determine the image quality or characteristic that the extracted portions of the captured image are to analyzed for and to determine the tolerance value that the determined image quality or characteristic is to be compared to. The multi area region of interest extractor 160 then generates the defined image quality or characteristic and determines if the determined image or quality of characteristic indicates in comparison with the tolerance value, whether the light source defined by the multi area property data stored in the multi area property memory portion 133 needs to be adjusted. If not, the multi area region of interest extractor 160 indicates to the part program generator and/or executor 170 that the next part program instruction should be executed.

In contrast, if the multi area region interest extractor 160 determines that the selected light source needs to be adjusted, the multi area region of interested extractor 160 provides an indication to the input light intensity command value adjuster 180. In response, the light intensity command value adjuster 180 adjusts the current light intensity command value for the selected light source. The light intensity command value adjuster 180 then outputs the adjusted light intensity command value for the selected light source to the power supply 190 so that the light intensity output by the selected light source is adjusted.

As indicated above, in various exemplary embodiments, the selected image quality or characteristic is first driven toward the goal state stored in the multi area property memory portion 133. Then, the resulting value for the selected image quality or characteristic is compared to a failure threshold. In particular, in these exemplary embodiments, the multi area region of interest extractor 160 determines if the selected image quality or characteristic has reached the goal state stored in the multi area property memory portion 133. If the determination by the multi area region of interest extractor 160 indicates that the light intensity should be increased, the input light command value adjuster 180 increases the adjusted light intensity command value output to the power supply 190 to increase the light intensity output by the selected light source. In contrast, if the determination by the multi area region of interest extractor 160 indicates that the light intensity should be decreased, the input light command value adjuster 180 decreases the adjusted light intensity command value output to the power supply 190 to decrease the light intensity output by the selected light source. For example, when the selected image quality or characteristic is the measured average brightness contrast and the goal state stored in the multi area property memory portion 133 is to maximize the measured average brightness contrast between the regions of interest, either case may occur when the measured average brightness contrast has not yet achieved its maximum value.

Once the light intensity of the selected light source is adjusted, the camera system 260, under control of the controller 120, captures another image of the part and outputs the captured image over the signal line 262 to the input/output interface 110. The input/output interface 110, under control of the controller 120, stores the newly captured image in the image memory portion 135.

Then, the multi area region of interest extractor 160, under control of the controller 120, again extracts the portions of the newly captured image as defined by the multi area region of interest generator 150. The multi area region of interest extractor 160 then again determines if the selected image quality or characteristic of the extracted regions has reached the goal state stored in the multi area property memory portion 133. If so, the multi area region of interest extractor 160, under control of the controller 120, indicates to the part program generator and/or executor 170 that the next part program instruction should be executed. Additionally, if the selected light source was adjusted with any other active light sources turned off, those light sources are turned back on. In particular, the input light command value adjuster 180 reads the stored values for any such other active light source from the previous settings memory portion 134 and outputs the restored input light command value to the power supply 190. Otherwise, the light source adjustment described above is repeated and a further new image is captured. This process then repeats until the image quality of the extracted portions of the captured image reaches the goal state stored in the multi area property memory portion 133.

As indicated above, in various other exemplary embodiments, the selected image quality or characteristic is compared to a success threshold, or tolerance value, stored in the multi area property memory portion 133 until the value of the selected image quality or characteristic is within the success threshold or tolerance value. In particular, if the comparison of the selected image quality or characteristic to the tolerance value determine by the multi area region of interest extractor 160 indicates that the light intensity should be increased, the input light command value adjuster 180 increases the command value output to the power supply 190 to increase the light intensity output by the selected light source. In contrast, if the comparison by the multi area region of interest extractor 160 indicates that the light intensity should be decreased, the input light command value adjuster 180 decreases the adjusted light intensity command value output to the power supply 190 to decrease the light intensity output by the selected light source.

For example, when the selected image quality or characteristic is the measured average brightness contrast and the goal state stored in the multi area property memory portion 133 is to place the measured average brightness contrast between the regions of interest above the tolerance value, either case may occur when the measured average brightness contrast is not yet above the tolerance value. Thus, if the comparison of the selected image quality or characteristic to the tolerance value indicates that the light intensity should be decreased, the input light command value adjuster 180 decreases the command value output to the power supply 190 to decrease the light intensity output by the selected light source.

Once the light intensity of the selected light source is adjusted, the camera system 260, under control of the controller 120, captures another image of the part and outputs the captured image over the signal line 262 to the input/output interface 110. The input/output interface 110, under control of the controller 120, stores the newly captured image in the image memory portion 135.

Then, the multi area region of interest extractor 160, under control of the controller 120, again extracts the portions of the newly captured image as defined by the multi area region of interest generator 150. The multi area region of interest extractor 160 then again determines if the selected image quality or characteristic of the extracted regions falls within the tolerance value defined in the part program. If so, the multi area region of interest extractor 160, under control of the controller 120, indicates to the part program generator and/or executor 170 that the next part program instruction should be executed. Additionally, if the selected light source was adjusted with any other active light sources turned off, those light sources are turned back on. In particular, the input light command value adjuster 180 reads the stored values for any such other active light source from the previous settings memory portion 134 and outputs the restored input light command value to the power supply 190. Otherwise, the light source adjustment described above is repeated and a further new image is captured. This process then repeats until the image quality of the extracted portions of the captured image falls within the tolerance value defined in the part program instruction.

It should be appreciated that any one of the various light sources 220–240 described above can include a plurality of differently colored light sources. That is, for example, the stage light 220 can include a red light source, a green light source and a blue light source. Each of the red, blue and green light sources of the stage light 220 can be separately driven by the power source 190.

Accordingly, it should be appreciated that a selected light source in the multi area properties data stored in the multi area properties memory portion cannot only indicate a particular light source that is to be adjusted, but can also indicate a particular color of a multi-color light source that is to be adjusted. Thus, if the image quality is to be determined based solely on the illumination provided by the selected light source, turning off the other light sources would include turning off the other colors of a multi-color light source.

Figure 7:
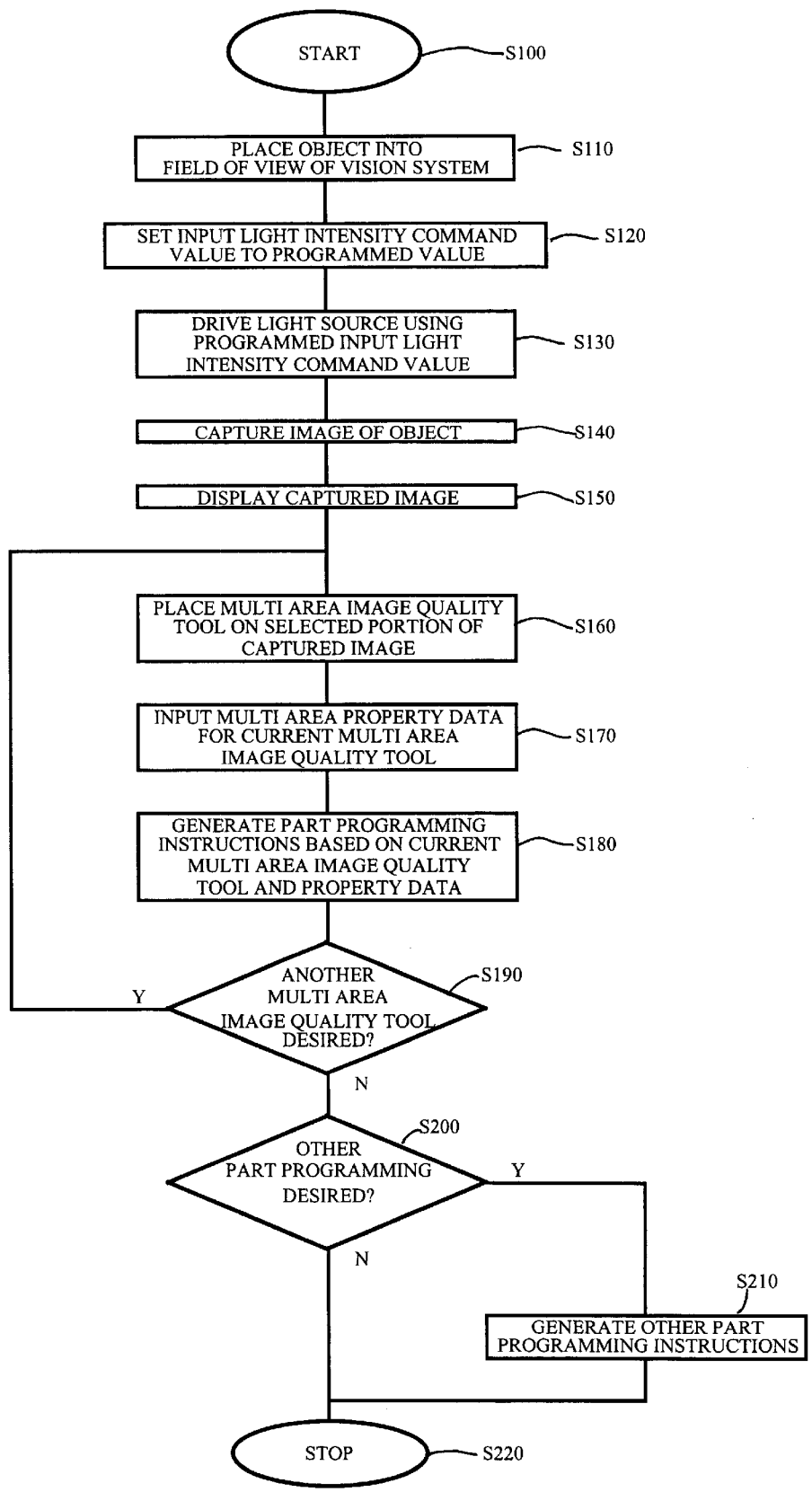
FIG. 7 is a flowchart outlining one exemplary embodiment of a method for placing an instance of a multi area image quality into a part program according to this invention.

FIG. 7 is a flowchart outlining one exemplary embodiment of a method for generating a part program instruction using the multi area image quality tool according to this invention. Beginning in step S100, control continues to step S110, where the user places an object to be viewed using a vision system into the field of view of the vision system. Next, in step S120, the user generates a part program instruction setting the light intensity command value for one or more of the light sources of the vision system. The input light intensity command values for the one or more selected light sources are set to the programmed values. Of course, it should be appreciated that, if the user has already generated such part program instructions, step S120 can be omitted and the light intensity command values for the one or more selected light sources are simply left at the previously programmed values. Of course, it should be appreciated that, if the user has previously placed the object into the field of view of the vision system and begun generating the part run of the instructions, step S110, and possibly step S120, can be omitted. Control then continues to step S130.

In step S130, the one or more selected light sources are driven using the programmed input light intensity command values. Next, in step S140, an image of the object is captured as illuminated by the one or more selected light sources when driven at the programmed input light intensity command values. Then, in step S150, the captured image is displayed. As above, if the image of the object was previously captured and displayed, steps S110–S150 can be omitted.

In step S160, the user places the multi area image quality tool on the selected portion of the captured image. As described above, the multi area image quality tool is placed on the captured image such that the bar of the multi area image quality tool extends across a critical feature of the captured image, such that the plurality of regions of interest of the multi area image quality tool are placed adjacent to and around the critical feature. In addition, when placing the multi area image quality tool on the selected portion of the captured image, the user scales the dimensions of the multi area image quality tool to the user desired values. Control then continues to step S170.

In step S170, the user inputs the multi area property data for the current multi area image quality tool. As indicated above, this multi area property data includes the selected light source to be adjusted, the selected image quality or qualities to be determined using the multi area image quality tool, whether the selected image quality is to be determined using only the selected light source or all active light sources, whether the image data in the regions of interest is to be filtered, and/or the tolerance value for the selected image quality. Next, in step S180, one or more part programming instructions are generated based on the location and dimensions of the current multi area image quality tool and the input multi area property data. Next, in step S190, a determination is made whether the user desires to generate another multi area image quality tool for the current captured image. If so, control jumps back to step S160. Otherwise, control continues to step S200.

In step S200, a determination is made whether other part programming instructions are desired. If so, control continues to step S210. Otherwise, control jumps to step S220. In the step S210, other part programming sections are generated. In particular, if such other part programming instructions include additional multi area image quality tools for different captured images of the object, steps S140–S200, and possibly steps S120 and S130, can be repeated as part of step S210. Once all of the desired other part programming instructions have been generated, control continues to step S220, where the method ends.

Figure 8A:
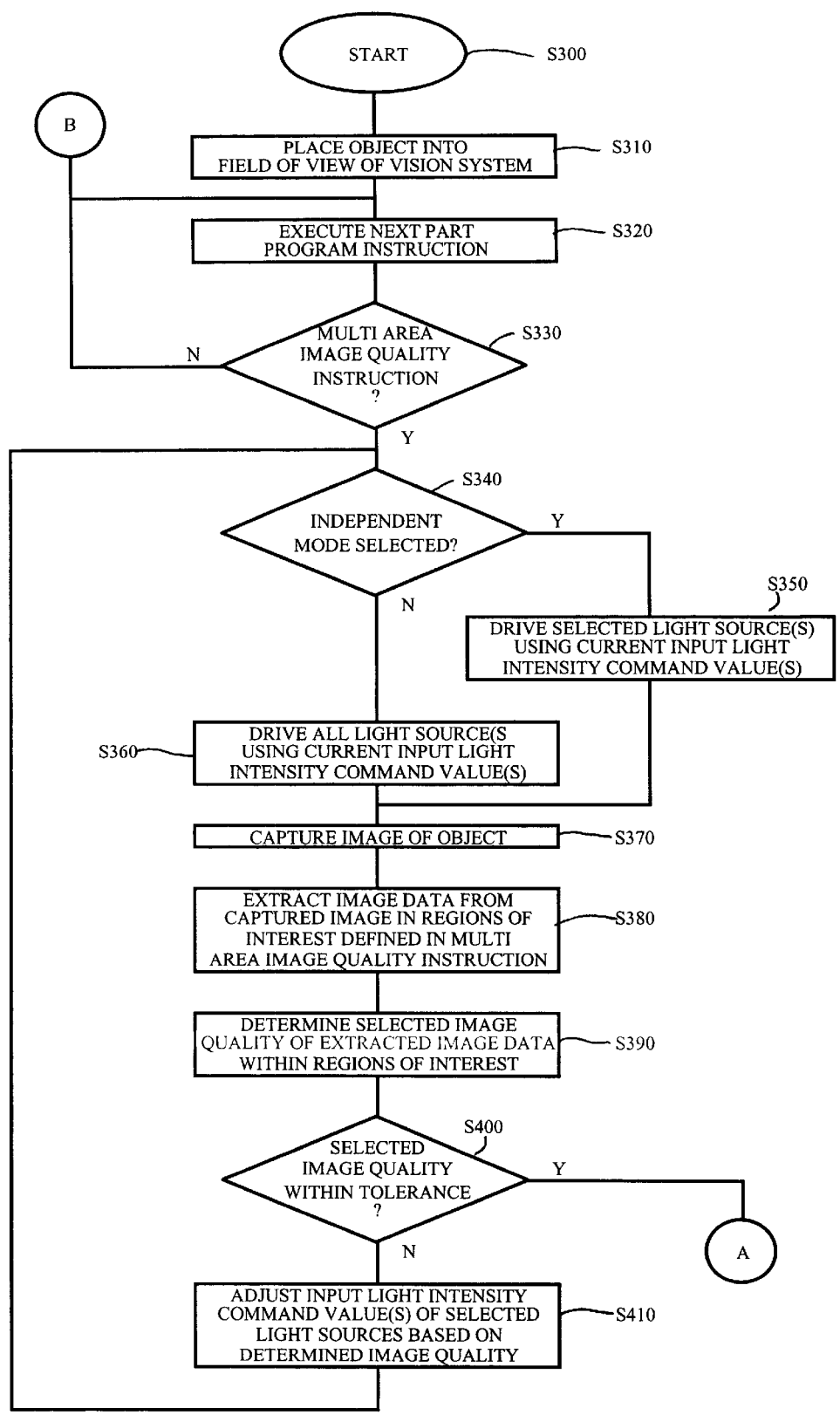
FIGS. 8A and 8B are flowcharts outlining one exemplary embodiment of a method for adjusting the lighting of a vision system relative to a critical region of an image according to this invention.
Figure 8B:
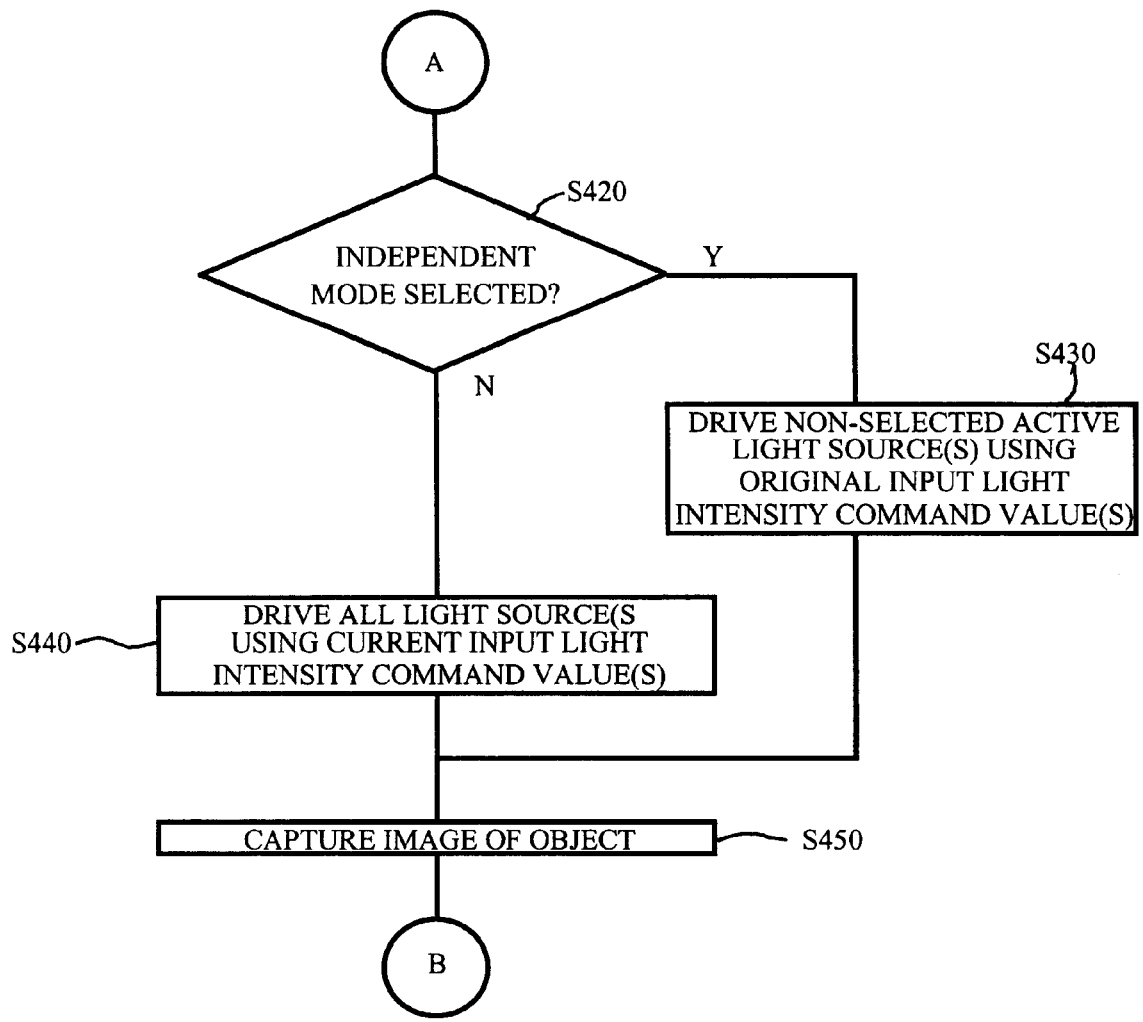

FIGS. 8A and 8B outline one exemplary embodiment of a method for executing a part programming instruction has been generated using the multi area image quality tool according to this invention. Beginning in step S300, control continues to step S310, where an object to be viewed by the vision system is placed into the field of view of the image system. Next, in step S320, the first or next part programming instruction of the currently executing part program is executed. Then, in step S330, a determination is made whether a multi area image quality instruction has been executed. If so, control continues to step S340. If not, control jumps back to step S320.

In step S340, a determination is made whether an independent mode, where only the selected light source or sources are used to illuminate the object has been selected, or whether a dependent mode, where all of the active light sources are used to illuminate the object, has been selected. If the independent mode has been selected, control continues to step S350. Otherwise, control jumps to step S360.

In step S350, only the selected light sources selected in the multi area image quality instruction are driven using the current input light intensity command values for the selected light sources as previously defined in one or more previously executed part programming instructions. Control then jumps to step S370. In contrast, in step S360, all the active light sources are driven using the current input light intensity command values as previously defined in one or more previous part program instructions. Control then continues to step S370.

In step S370, an image of the object is captured. Then, in step S380, image data is extracted from the captured image in the regions of interest defined in the multi area image quality instruction being executed. Next, in step S390, the image quality selected in the currently executing multi area image quality instruction is determined for the extracted image data within the defined regions of interest. Control then continues to step S400.

In step S400, a determination is made whether the selected image quality is within the tolerance range or value defined in the currently executing multi area image quality instruction. If so, control jumps to step S420. Otherwise, control continues to step S410. In step S410, the input light intensity command values of the one or more selected light sources are adjusted based on the determined image quality. Control then jumps back to step S340.

In contrast, in step S420, a determination is again made whether the independent mode is selected. If so, control continues to step S430. Otherwise control jumps to step S440.

In step S430, the non-selected active light sources, if any, are driven using the original input light intensity command values previously defined in one or more previously executed part programming instructions, while the selected light sources are continued to be driven using the adjusted input light intensity command values. Control then jumps to step S450. In contrast, in step S440, all of the light sources are driven using the current input light intensity command values. Thus, the non-selected active light sources are continued to be driven using the previously commanded light intensity command values while the selected light source is continued to be driven using the adjusted light intensity command values for the selected light sources. Control then continues to step S450.

In step S450, an image of the object is captured using the current light intensity command values, including the adjusted light intensity command value(s) for the selected light source(s). Control then jumps back to step S320, where the next part program instruction is executed.

It should be appreciated that the foregoing description of the systems and methods of this invention is based on automatic program operation. The systems and methods of this invention operate substantially the same when the illumination commands are issued manually through the one or more input devices 104 during manual or stepwise operation of the vision system 10.

The control system 100 can be implemented on a programmed general purpose computer. However, the control system 100 can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowcharts shown in FIGS. 7, 8A and 8B can be used to implement the control system 100.

It should be understood that each of the control circuits or elements of the control system 100 shown in FIG. 1 can be implemented as portions of a suitably programmed general purpose computer. Alternatively, each of the control circuits or elements of the control system 100 shown in FIG. 1 can be implemented as physically distinct hardware circuits within an ASIC, or using a FPGA, a PLD, a PLA or a PAL, or using discrete logic elements or discrete circuit elements. The particular form each of the control circuits or elements of the control system 100 shown in FIG. 1 will take is a design choice and will be obvious and predicable to those skilled in the art.

Moreover, the control system 100 can be implemented as software executing on a programmed general purpose computer, a special purpose computer, a microprocessor or the like. In this case, the control system 100 can also be implemented by physically incorporating it into a software and/or hardware system, such as the hardware and software systems of a vision system.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A method of adjusting lighting of a critical region of an object based on an image of the object, the image generated using a vision system including a controllable lighting system and an imaging system, the method comprising:

illuminating the object with the controllable lighting system in a first state;

obtaining an image of the object;

extracting image data of the image corresponding to at least a first region of interest of the image and a second region of interest of the image, the first and second regions of interest located relative to the critical region;

determining at least one image quality of the extracted image data; and adjusting the state of the controllable lighting system until the at least one image quality of the extracted image data satisfies a selected relationship.

2. The method of claim 1, further comprising repeating the obtaining, extracting, determining and adjusting steps until the image quality of the extracted image data satisfies the selected relationship.

3. The method of claim 1, wherein:

the controllable lighting system comprises a plurality of selectable light sources, each one light source having a controllable light intensity, and adjusting the state of the controllable lighting system includes at least one of:

selecting at least one of the plurality of selectable light sources, and adjusting the controllable light intensity of at least one of at least one selected light source.

4. The method of claim 1, wherein:

the controllable lighting system comprises a focusing sub-system; and adjusting the state of the controllable lighting system comprises adjusting the focusing sub-system.

5. The method of claim 1, further comprising, after adjusting the state of the controllable lighting system so that the at least one image quality of the extracted image data satisfies the selected relationship:

extracting image data from the critical region of the image; and processing the image data extracted from the critical region.

6. The method of claim 5, wherein:

the critical region includes an edge; and processing the image data extracted from the critical region comprises analyzing the image data extracted from the critical region to determine a location of the edge.

7. The method of claim 1 wherein the at least one image quality is at least one of contrast and brightness.

8. The method of claim 7, wherein the image quality is the contrast and the selected relationship maximizes a difference in contrast between the image data corresponding to the first and second regions of interest.

9. The method of claim 1, wherein the vision system further comprises a graphical user interface comprising a display portion that displays the obtained image of the object, the method further comprising displaying a graphical user interface widget representing the at least first and second regions of interest superimposed on the obtained image of the object.

10. The method of claim 9, wherein the graphical user interface widget is selectable, the method further comprising:

selecting the graphical user interface widget; and adjusting at least one of a location of the at least first and second regions of interest and an extent of the at least first and second regions of interest based on an input received from a user of the graphical user interface.

11. The method of claim 1, wherein the vision system further comprises a computerized control system, and at least one step of the method is executed automatically under the instructions of a program that automatically controls the vision system.

12. The method of claim 1, wherein the first and second regions of interest are located in a defined location relative to the critical region.

13. The method of claim 12, wherein the defined location relative to the critical region is one of a location adjacent to the critical region and a location spaced apart from the critical region but located within the image.

14. The method of claim 1, wherein at least one region of interest is located such that at least a majority of that region of interest exhibits substantially uniform image intensity.

15. The method of claim 1, wherein at least one region of interest is located such that at least a majority of that region of interest exhibits a substantially homogeneous pattern corresponding to a portion of the object which exhibits a substantially uniform surface.

16. The method of claim 1, wherein the vision system further comprises a graphical user interface comprising a display portion that displays the obtained image of the object, the method further comprising displaying a graphical user interface widget representing a plurality of sets of boundary lines, each set of boundary lines defining the location and extent of one of the plurality of regions of interest on the image display, wherein each set of boundary lines are independently positionable on the image and display and the extent of each set of boundary lines are independently adjustable on the image display.

17. The method of claim 16, wherein the graphical user interface widget is selectable, the method further comprising:

selecting the graphical user interface widget; and adjusting at least one of the location of one of the plurality of regions of interest and the extent of one of the plurality of regions of interest based on an input received from a user of the graphical user interface.

18. In a vision system including a controllable lighting system, an imaging system, a processor, and a display device on which image data is displayed; a graphical user interface widget displayable on the display device and useable to represent a plurality of regions of interest of an image, image data from the at least first and second regions of interest used to control the controllable lighting system, the graphical user interface widget comprising:

a plurality of sets of boundary lines, each set of boundary lines defining the location and extent of one of the plurality of regions of interest on the image display;

each set of boundary lines independently positionable on the image display; and the extent of each set of boundary lines independently adjustable on the image display.

19. The graphical user interface widget of claim 18, wherein the graphical user interface widget is placed in an initial configuration on the image display based on a point on the image provided to the processor by a user of the vision system.

20. The graphical user interface widget of claim 18, further comprising an indicator of the plurality of regions of interest included in a specific instance of the graphical user interface widget.

21. The graphical user interface widget of claim 20, wherein the indicator is at least one of a line extending between the regions of interest, a set of lines extending between the regions of interest, and a unique color for the boundary lines of the regions of interest included in a specific instance of the graphical user interface widget.

* * * * *